US00PP14881P2

(12) United States Plant Patent

Mowrey et al.

(10) Patent No.: US PP14,881 P2
(45) Date of Patent: Jun. 8, 2004

(54) PLUM TREE NAMED "SUPLUMTHIRTYFOUR"

(50) Latin Name: *Prunus salicina*
Varietal Denomination: Suplumthirtyfour

(75) Inventors: Bruce D. Mowrey, Watsonville, CA (US); David W. Cain, Bakersfield, CA (US); Terry A. Bacon, Bakersfield, CA (US)

(73) Assignee: Sun World International, Inc., Bakersfield, CA (US)

( * ) Notice: Subject to any disclaimer, the term of this patent is extended or adjusted under 35 U.S.C. 154(b) by 0 days.

(21) Appl. No.: 10/464,616

(22) Filed: Jun. 17, 2003

(51) Int. Cl.[7] ..... A01H 5/00
(52) U.S. Cl. ..... Plt./184
(58) Field of Search ..... Plt./184

(56) References Cited

U.S. PATENT DOCUMENTS

PP7,827 P 3/1992 Chamberlin, Sr.

*Primary Examiner*—Bruce R. Campell
*Assistant Examiner*—W C Haas
(74) *Attorney, Agent, or Firm*—Knobbe, Martens, Olson & Bear, LLP

(57) ABSTRACT

A new and distinct plum variety that possesses heavy and consistent production of large, firm, juicy fruit with an excellent eating quality. The fruit has a smooth, red-colored, slightly tart skin and yellow flesh color.

1 Drawing Sheet

Latin name of the genus and species of the plant claimed: *Prunus salicina.*
Variety denomination: 'Suplumthirtyfour'.

BACKGROUND AND SUMMARY OF THE INVENTION

The present invention relates to the discovery and asexual propagation of a new and distinct cultivar of Plum Tree, herein after referred to by the cultivar name 'Suplumthirtyfour'. The variety originated by hybridization. The variety was first hybridized and selected by Bruce Mowrey. The new variety was first evaluated by David Cain on Sun World Experimental Ranch 75 near Wasco, Calif. in Kern County. The new variety is characterized by heavy and consistent production of large, firm fruit of about 65 mm in diameter. The fruit of 'Suplumthirtyfour' have a smooth, red-colored skin with a yellow flesh color, ripening during the first half of October in the Bakersfield, Calif. area. The eating quality of 'Suplumthirtyfour' fruit is excellent with 19° brix, plentiful juice, and slightly tart skin flavor.

The parent varieties were first crossed in 1993, with the date of planting of February, 1994, and the date of first flowering being March, 1996. The new plum variety was first asexually propagated by Terry Bacon near Wasco, Kern County, Calif. in December, 2001, by grafting onto Flordaguard rootstock.

The seed parent is Sun World breeding selection, '90P-072' (unpatented), which was selected from a progeny of 'Queen Anne' (unpatented) crossed with pollen from 'Simka' (unpatented). The new variety is distinguished from its seed parent by ripening 10 days earlier and having round-shaped fruit as compared to elongated fruit for the seed parent. The pollen parent was an unknown Sun World breeding selection.

The new variety most nearly resembles 'October Sun' (U.S. Plant Pat. No. 7,827). It may be distinguished from 'October Sun' by having larger fruit (65 mm compared to 61 mm diameter with 'October Sun') and ripening 18 days later.

Additionally, the new variety is clingstone while 'October Sun' is freestone.

The accompanying color photographic illustration shows typical specimens of the foliage and fruit of the present new plum variety. The illustration shows the upper and lower surface of the leaves, an exterior and sectional view of a fruit divided across its suture plane to show flesh color, pit cavity and the stone remaining in place. The photographic illustration was taken shortly after being picked (shipping ripe) and the colors are as nearly true as is reasonably possible in a color representation of this type.

The new plum variety cv. 'Suplumthirtyfour' has been shown to maintain its distinguishing characteristics.

BRIEF DESCRIPTION OF THE FIGURE

The accompanying color photographic illustration in FIG. 1 shows typical specimens of the foliage and fruit of the present new plum variety. The illustration shows the upper and lower surface of the leaves, an exterior and sectional view of a fruit divided across its suture plane to show flesh color, pit cavity and the stone remaining in place. The photographic illustration was taken shortly after being picked (shipping ripe) and the colors are as nearly true as is reasonably possible in a color representation of this type.

DETAILED BOTANICAL DESCRIPTION OF THE INVENTION

Figure 1:
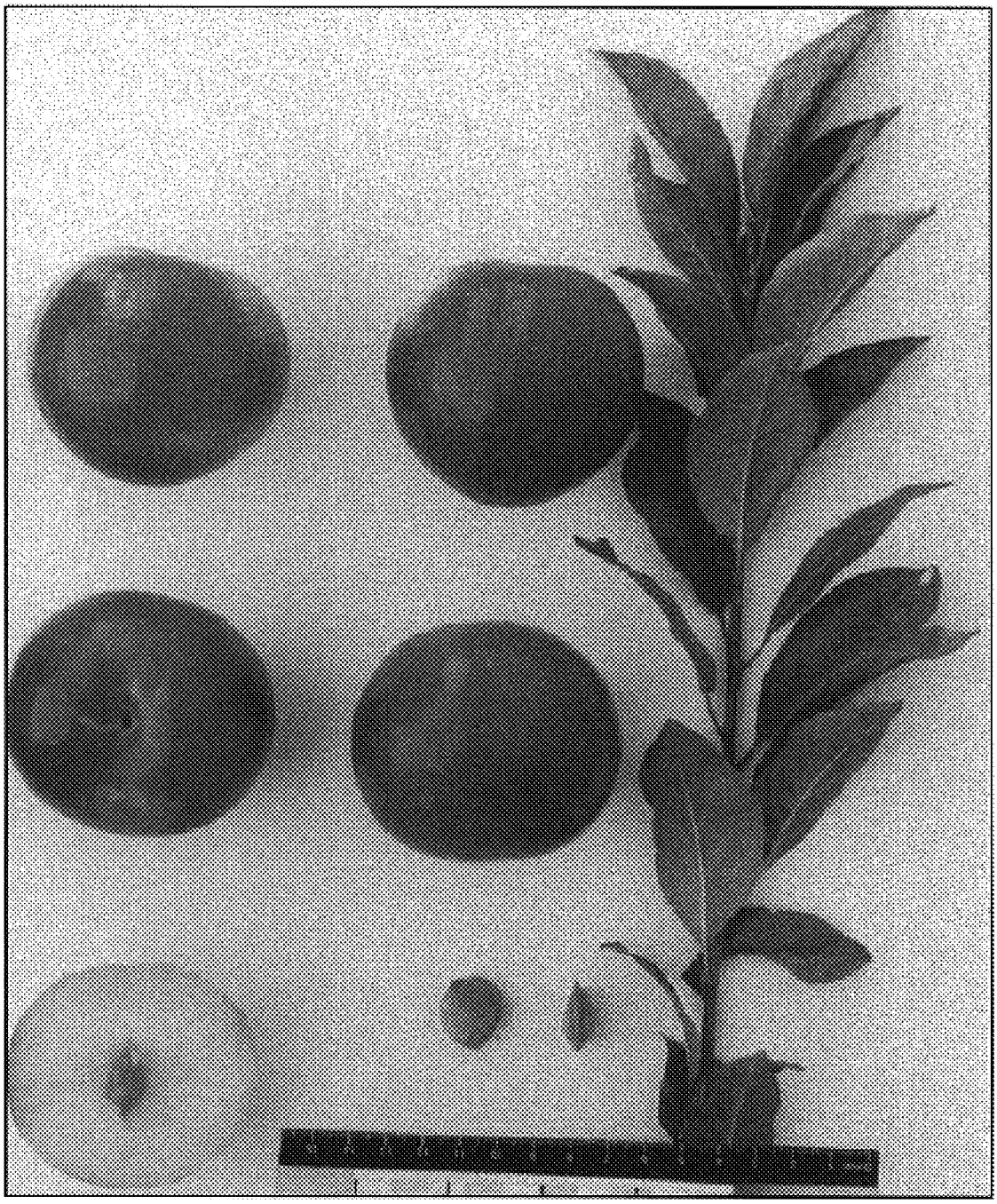

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England.

The descriptive matter which follows pertains to 8 year old trees grown in the vicinity of Wasco, Kern County, Calif., during 2002, and is believed to apply to plants of the variety grown under similar conditions of soil and climate elsewhere.

TREE (Measurements taken on an 8 year old tree)

General:

*Size.*—Medium. Normal for most plum varieties. Reaches a height of approximately 3–4 meters including normal pruning.

*Vigor.*—Vigorous; Growth of approximately 1.8 to 2 meters height the first growing season.

*Growth.*—Upright-spreading.

*Productivity.*—Productive. Fruit set is usually two or more times desired amount for marketable size fruit. Thinning and spacing of fruit is necessary.

*Form.*—Vase formed.

*Fruit bearing.*—Regular. No alternate bearing observed.

*Fertility.*—Somewhat self-fertile but pollinizer improves fruit set.

*Density of foliage.*—Dense. Pruning is required to open tree vase shape, allowing more sunlight to center of tree.

*Hardiness.*—Hardy in all fruit growing areas of California.

*Winter chilling requirement.*—Approximately 750 hours at or below 7.2° C.

*Tree resistance/susceptibility.*—No specific testing for relative plant disease resistance/susceptibility has been designed. Under close observation in Kern County, Calif., no particular plant/fruit disease resistance/susceptibility has been observed.

*Root stock.*—Flordaguard.

Trunk: (measurements at 30 cm above soil line).

*Diameter.*—Approximately 22 cm. Varies with soil type, fertility, climatic conditions and cultural practices.

*Surface texture.*—Medium shaggy, increases with age of tree.

*Color.*—About Greyed-orange 164B in recesses of the bark, and about Greyed-green 198D to Grey-brown 199B on the surface of the bark. Becomes darker with age.

Branches: (measurements at 90 cm above soil line).

*Diameter.*—Ranges from approximately 8 to 11 cm.

*Surface texture.*—Smooth on 1st year wood, increasing roughness with tree age.

*Color.*—Branches are about Greyed-orange 164B in recesses of the bark, and about Greyed-green 198C to Greyed-orange 176D on the surface of the bark.

Lenticels:

*Number.*—Few.

*Length.*—Approximately 5 mm.

*Width.*—Approximately 2 mm.

*Color.*—About Greyed-green 197D.

LEAVES (Data taken in July on fully expanded leaf at midpoint of current-season growth)

General:

*Average length.*—Approximately 68 mm.

*Average width.*—Approximately 33 mm.

*Form.*—Elliptic.

*Leaf blade tip.*—Cuspidate.

*Leaf base.*—V-shaped.

*Margin.*—Crenate.

*Venation.*—Pinnately net veined.

*Thickness.*—Medium.

*Color of upper surface.*—Green 137A.

*Color of lower surface.*—Green 138B.

*Surface texture.*—Smooth.

Petiole:

*Length.*—Approximately 12 mm.

*Diameter.*—Approximately 1 mm.

*Color.*—About Green 139D.

Glands:

*Average number.*—Eglandular.

Stipules:

*Number of stipules per bud.*—Two.

*Length.*—Ranges from Approximately 4 to 6 mm.

FLOWERING SHOOTS (Data taken in July at midpoint of current-season growth)

General:

*Diameter.*—Approximately 4 mm.

*Color.*—About Yellow-green 144B, turning about Yellow-green 152C as the wood matures.

Flowering shoot leaf buds:

*Shape.*—Ovoid.

*Length.*—Approximately 1 mm.

*Width.*—Approximately 1 mm.

*Color.*—About Greyed-orange 175B.

Flowering shoot flower buds:

*Number per node.*—Approximately 2 to 4.

*Shape.*—Ovoid.

*Length.*—Approximately 2 mm.

*Width.*—Approximately 2 mm.

*Color.*—About Greyed-orange 175B.

Flowering shoot lenticels:

*Density.*—Plentiful.

FLOWERS

General:

*Date of first bloom.*—Mar. 2, 2002.

*Date of full bloom.*—Mar. 5, 2002.

*Size (diameter of the fully open flower).*—Approximately 26 mm.

*Flower aroma.*—Very slight.

Peduncle:

*Length.*—Approximately 9 mm.

*Diameter.*—Approximately 0.9 mm.

*Color.*—About Yellow-green 145B.

Petals:

*Number per flower.*—5.

*Arrangement.*—Slightly overlapping.

*Length.*—Approximately 11 mm.

*Width.*—Approximately 9 mm.

*Shape.*—Elliptical.

*Apex shape.*—Rounded.

*Base shape.*—Narrows at point of attachment.

*Color (fully opened flower).*—White.

*Surface texture.*—Smooth.

*Margins.*—Smooth.

Sepals:

*Number per flower.*—5.

*Length.*—Approximately 4 mm.

*Width.*—Approximately 3 mm.
*Shape.*—Broad obovate with slight tip.
*Color.*—About Yellow-green 144C.
*Surface texture.*—Slightly rippled.

Stamens:
*Number per flower.*—Approximately 19 (ranges from 18–20).
*Length.*—Approximately 7 mm.
*Filament color.*—White.
*Anther color (just before dehiscence).*—About Yellow-orange 20A.
*Pollen color.*—About Greyed-orange 168A.

Pistil:
*Number of pistils per typical flower.*—One.
*Frequency of supplementary pistils.*—Occasionally two.
*Pistil length.*—Approximately 10 mm.
*Pubescence.*—None.
*Ovary diameter.*—Approximately 1.2 mm.
*Stigma position in relation to anthers.*—Stigma extends below anthers.

FRUIT

General: (data taken at firm-ripe stage on mature tree managed to obtain maximum quality under conditions stated above).
*Harvest date of first pick.*—Oct. 8, 2002.
*Harvest date of last pick.*—Oct. 30, 2002.
*Length (stem end to apex).*—Approximately 65 mm.
*Diameter in line with suture plane.*—Approximately 65 mm.
*Diameter perpendicular to suture plane.*—Approximately 60 mm.
*Average weight.*—Approximately 130 gm.
*Shape viewed from apex.*—Nearly rounded, symmetrical.
*Shape viewed from side, facing suture.*—Rounded, with apex slightly extended. Symmetrical.
*Shape viewed from side, perpendicular to suture.*—Rounded, with apex slightly extended. Symmetrical.
*Fruit apex shape.*—Rounded to slightly extending.
*Fruit stem-end cavity depth.*—Shallow.

Stem:
*Length.*—Approximately 9 mm.
*Diameter.*—Approximately 2 mm.
*Color.*—About Green 143C.

Skin:
*Thickness.*—Medium.
*Adherence to flesh.*—Tenacious.
*Surface texture.*—Smooth.
*Pubescence.*—None.
*Bloom.*—Moderate amount.
*Ground color.*—Remains on fruit shoulders; about Yellow-green 154C.
*Overcolor.*—Covers about 85% of ftuit surface, about Red 46A.
*Taste.*—Mildly tart to neutral.

Flesh:
*Color.*—About Yellow-orange 19C, slightly darker at perimeter and pit cavity.
*Texture.*—Fine textured and firm.
*Ripens.*—Evenly.
*Fibers.*—Few.
*Flavor.*—Sweet with low acidity.
*Aroma.*—Moderate.
*Brix.*—Approximately 19 degrees.
*Juice.*—Plentiful.
*Use.*—Dessert. Market, local and long distance.
*Keeping and shipping quality.*—Good. Holds well in cold storage for approximately 6 weeks and maintains good firmness and eating quality. Minimal bruising and scarring in packing and shipping trials.

STONE (Measurements taken on dried stones)

General:
*Adherence to flesh.*—Clingstone.
*Length.*—Approximately 19 mm.
*Diameter in line with suture plane.*—Approximately 20 mm.
*Diameter perpendicular to suture plane.*—Approximately 9 mm.
*Form (viewed from broad side).*—Rounded. Asymmetrical because of prominent keel.
*Form (viewed from stem end).*—Oval, nearly symmetrical.
*Base shape.*—Flattened, retuse at stem attachment.
*Apex shape.*—Rounded with a small dull point.
*Stone surface.*—Irregularly furrowed near base. Lightly ridged toward base. Lightly pitted throughout.
*Comparison of stone halves.*—Nearly equal.
*Ridges.*—One on each side of the suture, small and rounded, beginning at the base and extending throughout the length of the stone.
*Stone outgrowing keel.*—Well developed.
*Tendency to split.*—None.
*Stone color when dried.*—About Greyed-yellow 162B.

What is claimed is:

1. A new and distinct plum tree named 'Suplumthirtyfour' as herein described and illustrated.

* * * * *